United States Patent
Gray, III (10) Patent No.: US 10,521,558 B2
(45) Date of Patent: Dec. 31, 2019

(54) SYSTEMS AND METHODS FOR DELIVERING REMEDY FREQUENCIES

(71) Applicants: William Edwin Gray, III, Los Gatos, CA (US); COHERENCE APPS, LLC, Los Gatos, CA (US)

(72) Inventor: William Edwin Gray, III, Los Gatos, CA (US)

(73) Assignee: COHERENCE APPS, LLC, Los Gatos, CA (US)

( * ) Notice: Subject to any disclaimer, the term of this patent is extended or adjusted under 35 U.S.C. 154(b) by 255 days.

(21) Appl. No.: 15/320,320

(22) PCT Filed: Jun. 20, 2015

(86) PCT No.: PCT/US2015/036839
§ 371 (c)(1),
(2) Date: Dec. 20, 2016

(87) PCT Pub. No.: WO2015/200145
PCT Pub. Date: Dec. 30, 2015

(65) Prior Publication Data
US 2017/0277839 A1  Sep. 28, 2017

Related U.S. Application Data

(60) Provisional application No. 62/018,214, filed on Jun. 27, 2014.

(51) Int. Cl.
*G06F 19/00* (2018.01)
*A61B 5/16* (2006.01)
(Continued)

(52) U.S. Cl.
CPC ............. *G06F 19/34* (2013.01); *A61B 5/165* (2013.01); *A61J 1/065* (2013.01); *A61J 1/05* (2013.01);
(Continued)

(58) Field of Classification Search
CPC .......... A61J 1/065; A61J 1/18; A61J 2205/60; A61J 1/05; G06F 19/3481; G06F 19/34; Y02A 90/26; H04L 67/10; A61B 5/165
See application file for complete search history.

(56) References Cited

U.S. PATENT DOCUMENTS

2007/0166730 A1   7/2007  Menon et al.
2008/0150518 A1   6/2008  Edwin et al.
(Continued)

FOREIGN PATENT DOCUMENTS

EP   1981996 A2   10/2008
EP   2253954 A2   11/2010
(Continued)

OTHER PUBLICATIONS

International Search Report and Written Opinion for International Patent Application No. PCT/US2015/036839 dated Sep. 30, 2015, 12 Pages.

(Continued)

*Primary Examiner* — Christine H Matthews
*Assistant Examiner* — Joshua Daryl D Lannu
(74) *Attorney, Agent, or Firm* — EcoTech Law Group, P.C.

(57) ABSTRACT

A method of providing a remedy is described. The method includes: (i) receiving, from a client device, answers to one or more of sets of questions that are relevant to one or more ailments and/or one or more unique expressions of the ailments; (ii) grading the answers using one or more remedy appropriateness values to produce graded answers, and wherein an remedy appropriateness value quantifies clinical importance of a remedy with respect to a question that is answered; (iii) scoring one or more remedies based on the graded answers to arrive at one or more remedy scores and identifying one or more top remedies that have high remedy (Continued)

scores; (iv) choosing, from a library of frequency files, one or more frequency files that correspond to one or more of the top remedies; and (v) presenting the frequency file as a remedy to the client device.

15 Claims, 3 Drawing Sheets

(51) Int. Cl.
*A61J 1/06* (2006.01)
*A61J 1/18* (2006.01)
*A61J 1/05* (2006.01)
*H04L 29/08* (2006.01)

(52) U.S. Cl.
CPC .............. *A61J 1/18* (2013.01); *A61J 2205/60* (2013.01); *H04L 67/10* (2013.01)

(56) References Cited

U.S. PATENT DOCUMENTS

| | | |
|---|---|---|
| 2008/0162352 A1 | 7/2008 | Gizewski |
| 2011/0066004 A1 | 3/2011 | Sullivan et al. |
| 2013/0262357 A1 | 10/2013 | Amarasingham et al. |
| 2013/0285677 A1 | 10/2013 | Hammer |

FOREIGN PATENT DOCUMENTS

| | | | |
|---|---|---|---|
| WO | 2003104939 A2 | 12/2003 | |
| WO | WO-03104939 A2 * | 12/2003 | ............. G16H 10/20 |
| WO | 2014012356 A1 | 1/2014 | |

OTHER PUBLICATIONS

The Partial Supplementary European search report for the Application No. 15812709.2 dated Feb. 2, 2018, 11 pages.

* cited by examiner

SYSTEMS AND METHODS FOR DELIVERING REMEDY FREQUENCIES

RELATED APPLICATION

This application claims priority to U.S. provisional application No. 62/018,214, filed Jun. 27, 2014, and is incorporated by reference for all purposes.

FIELD

The present teachings relate generally to methods of producing personalized healing frequencies to treat ailments. More particularly, the present teachings relate to producing personalized healing frequencies selected from a library to treat ailments based on an ailing person's responses to certain questions.

BACKGROUND

Acute ailments such as fever, influenza, earaches, cholera, typhoid, malaria, and tuberculosis are prevalent throughout all cultures whether wealthy or impoverished. To this end, homeopathy is a two-century-old science of healing based on matching specific homeopathic remedies to individual patterns of symptoms that stem from acute ailments in each patient. Homeopathy spread rapidly throughout the world primarily for its effectiveness in acute ailments, its lack of toxicity, and its inexpensiveness. Homeopathic remedies are initially prepared by submitting a substance in solution to serial dilutions and vigorous shaking between each dilution, ultimately to a point beyond Avogadro's number. Modern research has proven that shaking and diluting produce nano-clusters, which carry the same complex energy frequencies belonging to the original substance.

SUMMARY

The present teachings provide a method for extracting a signal, e.g., electronic signal, from such liquids that may have homeopathic remedial or generally therapeutic value and also provide a method for providing an electronic signal to a client device, which may be accessed by homeopathic practitioner and/or an ailing individual.

In one aspect, the present teachings provide methods of providing a remedy. One such exemplar method includes: (i) receiving, from a client device, answers to one or more of sets of questions that are relevant to one or more ailments and/or one or more unique expressions of the ailments; (ii) grading the answers using one or more remedy appropriateness values (which may reside in a logic engine and may be assigned by a treatment provider, preferably a homeopathic practitioner) to produce graded answers, and wherein a remedy appropriateness value quantifies clinical importance of a remedy with respect to a question that is answered; (iii) scoring one or more remedies based on the graded answers to arrive at one or more remedy scores and identifying one or more top remedies that have high remedy scores; (iv) choosing, from a library of frequency files, one or more frequency files that correspond to one or more of the top remedies; and (v) presenting the frequency file as a remedy to the client device. In one embodiment of the present teachings, before performing the receiving step, the method further includes the steps of: (i) identifying, based on responses to inquiries, one or more sets of questions that are relevant to one or more ailments and/or one or more unique expressions of the ailments; and (ii) presenting, to the client device, one or more of the set of questions that are identified as relevant. A set of questions typically includes multiple questions.

The above-mentioned step of identifying may include: (i) providing inquiries (e.g. in a tiered format) to the client device; and (ii) receiving, from the client device, response to the inquiries. Further, the step of providing may include providing multiple sets of inquiries in different instances in time, and a subsequent series of inquiries is provided based on answers responsive to a previous series of inquiries.

In preferred embodiments of the present methods of providing a remedy, the step of grading includes using another parameter—"question value" to produce the graded answer. The question value (may be a value that resides in the logic engine and may be assigned by a treatment provider, preferably a homeopathic practitioner), and quantifies importance of a particular question within a particular set of questions. In one example, for each question that is answered, the graded answer equals $1(Q \times R)$, where "Q" represents the question value and "R" represents the remedy appropriateness value. In another example, for each question that is answered, the graded answer equals $1(Q+R)$, where "Q" and "R" are the same variables as discussed previously.

There are numerous ways to implement the method of providing a remedy. By way of example, with respect to the step of scoring, each of the graded answers may be added to arrive at a remedy score. In another example, the step of presenting the frequency file includes transmitting a sound file that can be played at the client device, or in the alternate, includes producing a sound at the client device by playing the frequency file. In yet another example, the step of choosing includes selecting a top remedy that has the highest score among the remedies that are scored.

In an another embodiment of the present teachings, if one or more of top remedies have the same remedy score, then the method of providing the remedy further comprises: (i) providing, to the client device, one or more confirmatory questions, which are different from one or more of the sets of questions; (ii) receiving, from the client device, confirmatory answers to one or more of the confirmatory questions; (iii) grading confirmatory answers using one or more remedy appropriateness values (which quantifies clinical importance of a remedy with respect a confirmatory question that is answered) to produce graded confirmatory answers; (iv) scoring one or more of the top remedies based on the graded confirmatory answers to arrive at a confirmatory top remedy score; and (v) presenting, to the client device, a frequency file as a remedy, and that corresponds to the confirmatory top remedy score. The step of presenting the frequency file includes playing the frequency file for a specific duration and/or a specific frequency. The step of duration is a time period that is preferably a value between about 5 seconds and about 1 minute. The frequency is preferably played any number of times chosen from a group comprising certain number times per hour, hourly, certain times a day and daily.

In another aspect, the present teachings provide different designs of signal extraction systems. One such exemplar system includes: (i) a container holding a liquid; (ii) a coil that receives the container, and in response to presence of the liquid inside the container, the coil generates an analog signal; (iii) a signal converter that converts the analog signal to a digital signal; (iv) an amplifier that amplifies the digital signal to produce an amplified digital signal; (v) a format converter that converts the digital signal to a digitized file (which may be in .wav format).

In certain embodiments of the present arrangement, the signal extraction system further includes a faraday cage that houses the container and the coil. The faraday cage and/or the coil may be grounded. Not necessarily, but preferably, the coil is a random signal generator. In this preferred arrangement, the liquid is a solution that includes nanoparticles distributed inside distilled water, and the coil generates a signal in response to presence of the nanoparticles inside the distilled water.

In yet another aspect, the present teachings provide methods of signal extraction. One such exemplar method includes: (i) obtaining an analog signal produced, in response to presence of a liquid, at a coil; (ii) converting the analog signal to a digital signal; and (iii) converting the digital signal to a digitized file.

In one embodiment of the present teachings, the step of obtaining includes introducing a container holding the liquid inside the coil. In another embodiment, the present methods of extraction further include conveying the analog signal to a signal converter, and the step of conveying is carried out before the step of converting the analog signal to the digital signal. In a preferred embodiment of the present teachings, the step of converting the digital signal to the digitized file includes: (i) amplifying the digital signal to produce an amplified digital signal; and (ii) converting the amplified digital signal to a digitized file.

In yet another aspect, the present teachings provide other methods of signal extraction. One exemplar of such other methods includes: (i) obtaining a first analog signal produced, in response to presence of a liquid (e.g., preferably distilled water), at a coil, wherein the liquid includes nanoparticles distributed inside a liquid; (ii) converting the first analog signal to a first digital signal; (iii) obtaining a second analog signal produced, in response to presence of the liquid and in absence of the nanoparticles; (iv) converting the second analog signal to a second digital signal; (v) subtracting from the first digital signal the second digital signal to produce a digitized signal associated with the nanoparticles; and (vi) converting the digital signal associated with the nanoparticles to a digitized file.

In one implementation of this exemplar method, the step of subtracting includes: (i) amplifying the first digital signal to produce a first amplified digital signal; (ii) amplifying the second digital signal to produce a second amplified digital signal; and (iii) subtracting from the first amplified digital signal, the second amplified digital signal to produce the digitized signal associated with the nanoparticles. In preferred embodiment, this exemplar method further includes storing the digitized signal so that is may be used in a subsequent step. For example, digitized signal is stored as part of a library of sound files that are remedies to ailment.

DETAILED DESCRIPTION OF THE PREFERRED EMBODIMENTS

In the following description numerous specific details are set forth in order to provide a thorough understanding of the present invention. It will be apparent, however, to one skilled in the art that the present invention may be practiced without limitation to some or all of these specific details. In other instances, well known process steps have not been described in detail in order to not unnecessarily obscure the invention.

The present teachings propose selecting appropriate remedy signals based on the user's answers to predetermined questions, and then delivering the signals via a client device, e.g., a smartphone or a digital device, in ordinary sound frequency ranges in order to provide rapid relief from ailments. Effectiveness of such remedy signal delivery has been proven clinically in animals and humans. In a preferred embodiment of the present teachings, the signals are obtained from homeopathic remedies.

As explained below, the energy frequencies may be extracted and recorded as a sound file that may be in a MP3 format or .wav format. In some instances, sound files in .wav format represent a preferred embodiment of the present teachings as they maintain more subtlety to signals by avoiding compression loss.

Figure 1:
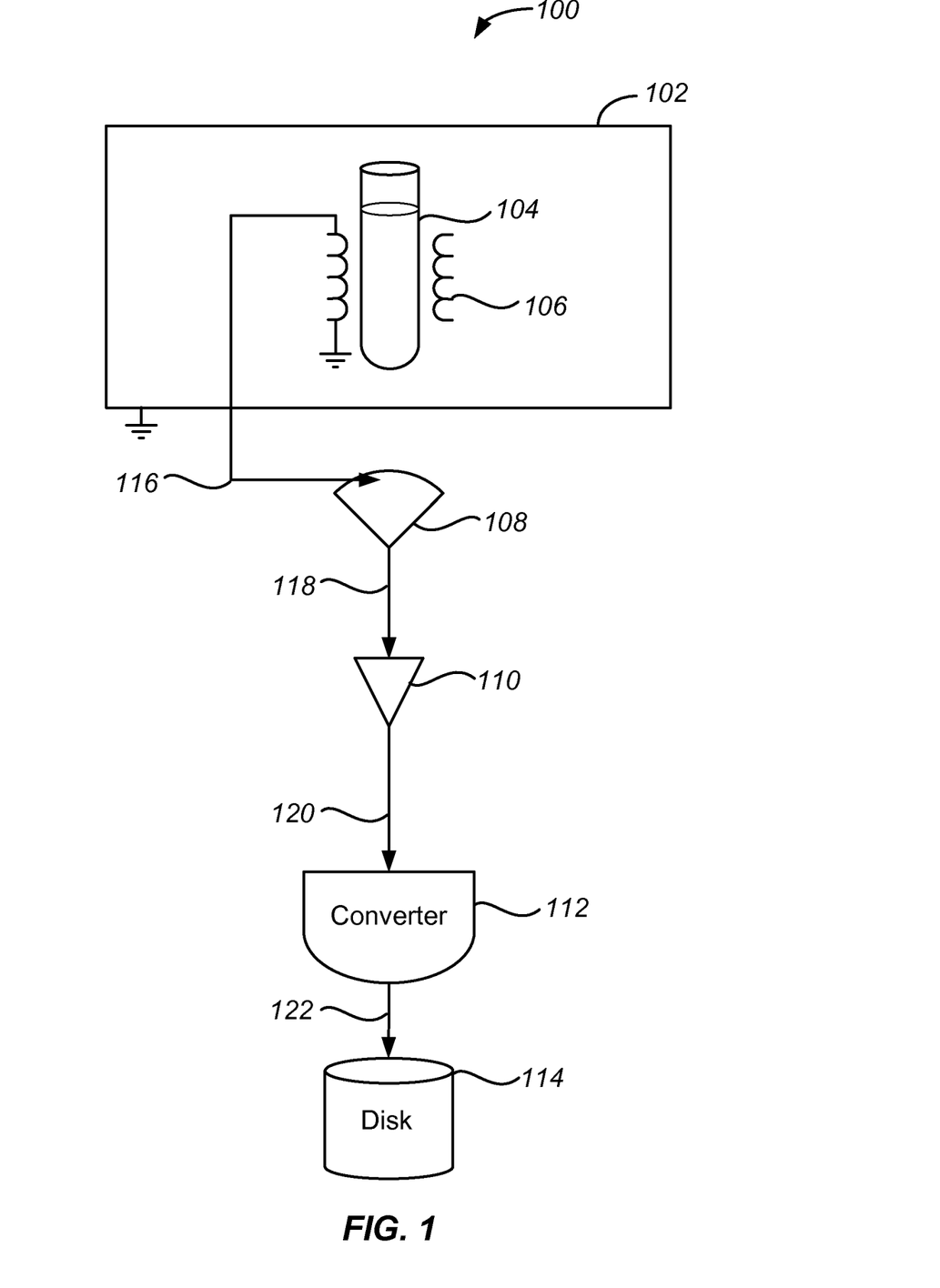
FIG. 1 shows a block diagram of a signal extraction system, according to one embodiment of the present arrangements and that extracts signals from a remedy, e.g., homeopathic remedy.

FIG. 1 shows a signal extraction system 100, according to one embodiment of the present invention and that extracts signals from a remedy, e.g., homeopathic remedy. Signal extraction system 100 includes a Faraday Cage 100, which in turn includes a test tube 102 that contains a sample of remedy, preferably homeopathic. Inside Faraday Cage 102, test tube 102 is positioned inside a coil 106. In one embodiment of the present arrangement, coil 106 and Faraday Cage 102 are both connected to ground.

A signal conveyance 116 conveys a signal generated at coil 106 to an analog-digital converter (hereinafter referred to as a "digitizer) 108. A digital signal produced at digitizer 108 is transmitted by a connection 118 to an amplifier 110 that amplifies the digital signal to produce an amplified digital signal. Another connection 120 conveys the amplified digital signal to a converter 112, which converts the amplified digital signal to a sound file. Using yet another connection 122, the sound file is stored in memory 114 (e.g., cloud memory or disk).

During operation of signal extraction system 100, a sample of remedy inside a test tube 104 is surrounded by or positioned inside a coil 106 that is arranged to generate an analog signal. In one embodiment of the present teachings, remedies, particularly those that are homeopathic based, radiate energy due to the presence of nanoparticles that are energized by succession enhanced by dilution. The configuration of coil 106 and test tube 104 is enclosed inside Faraday cage 102 and electricity that is captured by cage 102 may be grounded. Similarly, charge that accumulates at coil 106 may also be grounded.

The analog signal is converted to a digital signal by digitizer 108, which produces a digital signal that is transmitted via connection 118 to amplifier 110. At this stage, amplifier 110 amplifies the digital signal to produce an amplified digital signal that is sent through connection 120 to converter 112 where it is converted to a sound file, e.g., of .wav or MP3 format. Through communicative coupling 112 (which need not be a physical connection) the sound file is stored in memory 114.

In accordance with one embodiment of the present teachings, when a homeopathic remedy contained inside test tube 104 is positioned inside coil 106, amplifier 110 and digitizer 108 are played for any reasonable duration, e.g., as long as a few second to approximately one minute. The resulting digitized sound file is recorded via soundcard and computer software.

Figure 2A:
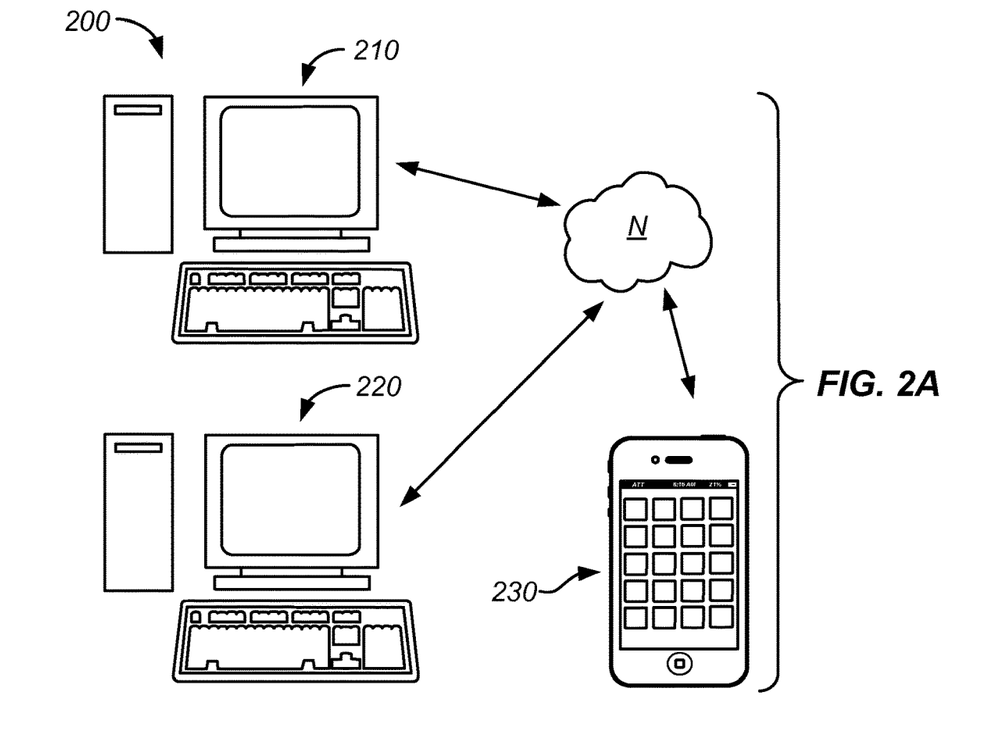
FIG. 2A shows a block diagram of a signal delivery system, according to one embodiment of the present arrangements, for delivering the extracted signal using a server to a client device.

By using this technique on different type of remedies, different digitized sound files are created to form a library of digitized sound files. FIG. 2, as discussed below, describes formation of such a library and retrieving and playing the appropriate remedy to have healing affects.

Figure 2B:
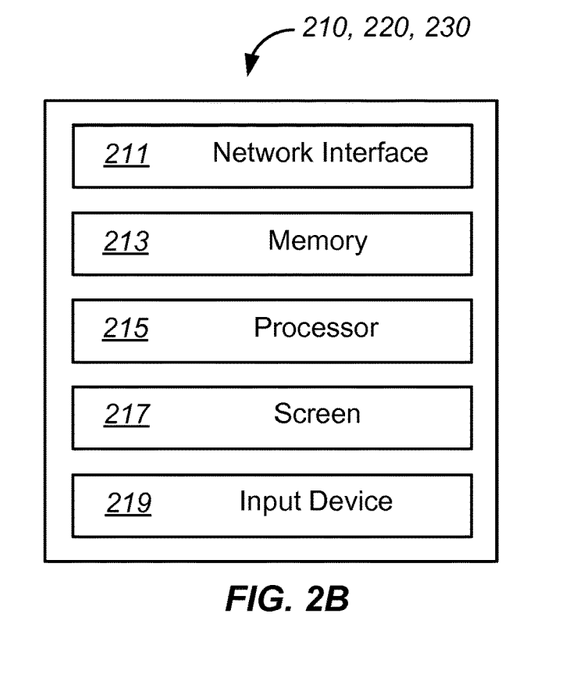
FIG. 2B shows a block diagram of the server, according to one embodiment of the present arrangements and that is shown in FIG. 2A.

FIG. 2A shows one embodiment of messaging system that includes a computer platform 200, which in turn includes a server 210 and a plurality of computers 220 and/or mobile devices 230 (one of each being shown in FIG. 2A) that are programmed to allow users to communicate over a network N. As shown in FIG. 2B, devices 210, 220, and 230 each include their own network interface 211, memory 213, processor 215, screen 217, and input device 219. In one embodiment, device 230 is a wireless device, and network N is allowed wireless communication to the device. In general, server 210 may include one or more computers and data storage devices, and may produce programming instructions, files, or data that may be transmitted over network N to user's devices 220 and 230 which may be used by a user to enter a protocol, to run a protocol, including entering data, and/or analyzing data stored on server 210.

Server 210 is a computer or network of computers. In one embodiment of the present teachings, network interface 211, memory 213, and processor 215 of server 210 are configured such that the processor executes a program stored in memory to accept input and/or provide output through the network interface over network N to devices 220 and/or 230. Although not necessary, but a logic engine, preferably a homeopathic logic engine, resides in processor 215. As will be explained later, the logic engine may have stored thereon certain parameters (e.g., remedy appropriateness values and in certain embodiments, questions values) that are used for grading answers that are received from the client device.

User devices 220 may be, for example and without limitation, a desktop or portable computer, and user device 230 which may be, for example and without limitation, a user device such as a cellular telephone, a portable digital assistant, a tablet, a stationary computing appliance including, but not limited to, a kiosk in a public or retail environment or some other wearable computing device. Network interface 211 of devices 220 and/or 230 is used to communicate with server 210 over a wireless network, which may be, for example and without limitation, a cellular telephone network, a WiFi network or a WiMax network or a Bluetooth network, and then to other telephones through a public switched telephone network (PSTN) or to a satellite, or over the Internet. Memory 213 of devices 220 and/or 230 includes programming required to operate device 230, such as an operating system or virtual machine instructions, and may include portions that store information or programming instructions obtained over network N, or that are input by the user. In one embodiment, screen 217 and input device 219 of mobile device 230 are physically combined as a touch screen 217/219, providing the functions of display and input.

In one embodiment, user device 220 and/or 230 is provided with programming that allows users to communicate with one another using a messaging system for sending, for example and without limitation, text and/or media to other users. Server 210 is an intermediary in the communication, and stores information regarding the messages.

Figure 3:
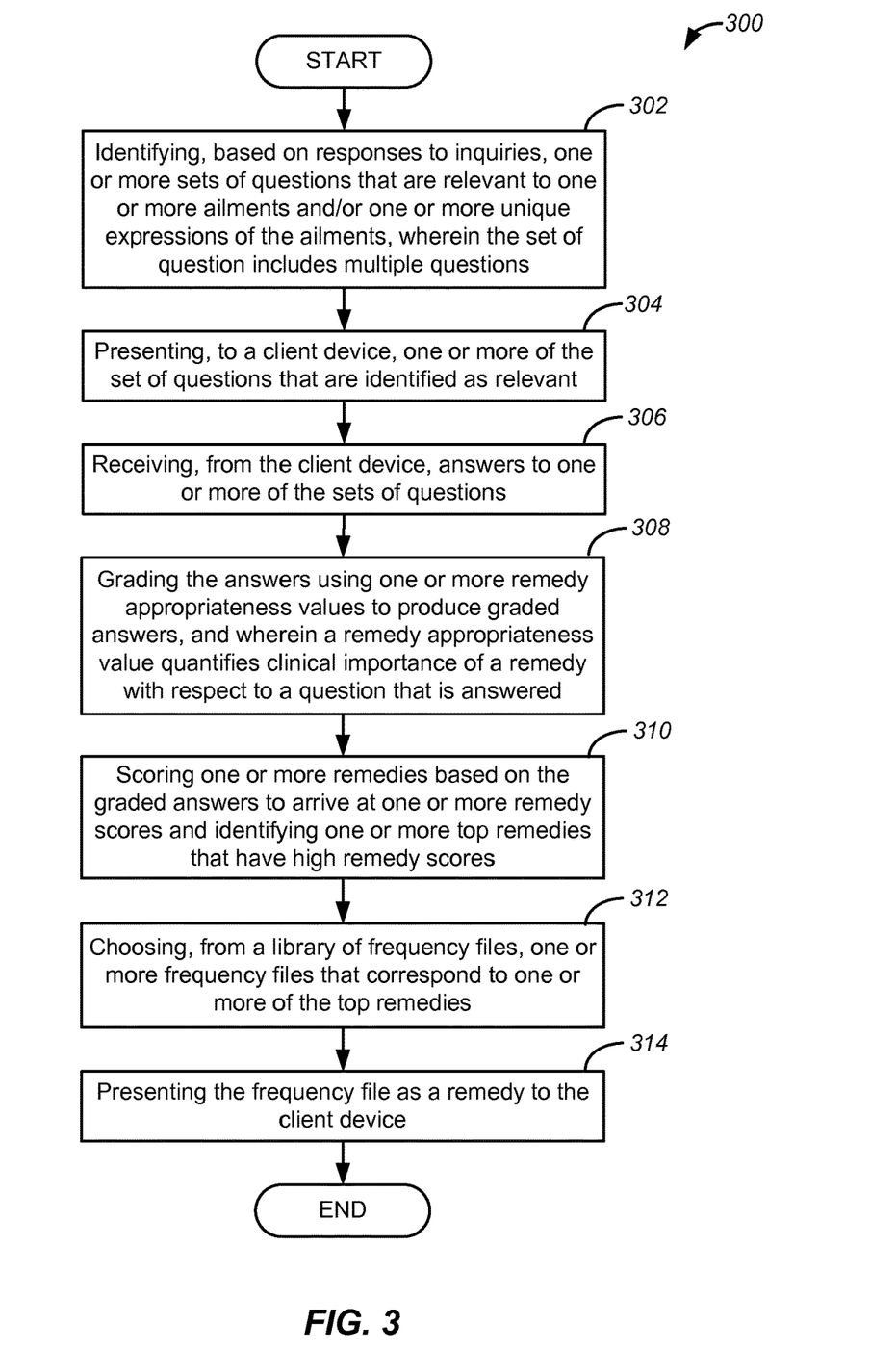
FIG. 3 shows a process flow diagram, according to one embodiment of the present teachings and that based on response from an ailing person selects a personalized remedy to treat an ailment from a library of remedies.

In certain embodiments, as noted above, system 200 includes several components, including but not limited to server 210 and a plurality of user devices 220 and 230, which are programmed to cooperatively achieve one or more of the following functions: 1) the operating of a messaging-like communication protocol (a "Messaging System") to provide content between server 230 and individual users, for example, of devices 220 and 230; 2) querying, through screens and input devices of devices 230, input indicative of a plurality of user's responses to inquiries and answers to one or more sets of questions, all of which are described below in connection with FIG. 3; and 3) presenting a frequency file (e.g., frequency file described in step 316 of FIG. 3) to devices 220 and 230.

FIG. 3 shows a process flow diagram 300, according to one embodiment of the present invention, for providing a frequency file as a remedy to an ailment. Process 300 may begin with a step 302, which includes identifying, based on responses to inquiries, one or more sets of questions that are relevant to one or more ailments and/or one or more unique expressions of the ailments. The set of questions includes multiple questions. In an alternate embodiment of the present teachings, before one or more of the relevant sets of questions are identified, additional steps are performed. In this embodiment, before the above-described step 302 is carried out, process 300 includes providing inquiries to and receiving responses to the inquiries from the client device. A user of the client devices includes, but is not limited to a homeopathic practitioner, a caregiver, and/or an ailing individual.

Table 1 shows exemplar inquiries and sets of questions, QS21, QS51 and QS79, presented to a client device when treating for anxiety. Although Table 1 shows 3 sets of questions, there may be more than 20 sets of questions associated with each inquiry.

TABLE 1

| | | | | | QS21 | QS51 | QS79 |
|---|---|---|---|---|---|---|---|
| What is the intensity of the anxiety? | | | | | | | |
| Moderate | What is your Age/Gender? | | | | | | |
| | I am 15 or below | | | | | | |
| | I am an adult female | Concomitants? | | | | X | |
| | | Emotional | | | | | X |
| | | Physical | More Concomitants? | | | | |
| | | | General | Modalities | | | |
| | | | | Yes | | | |
| | | | | No | | | |

TABLE 1-continued

| | | |
|---|---|---|
| | Neuromuscular | Modalities |
| | | Yes |
| | | No |
| | Cardiac | Modalities |
| | | Yes |
| | | No |
| | Gastrointestinal | Modalities |
| | | Yes |
| | | No |

In the example presented in Table 1, inquiries are directed to intensity (e.g., whether mild, moderate, or high level) of ailment, age and gender of ailing individual, emotional or physical manifestation of ailment, and presence of concomitants. If concomitants are deemed present, then it may be inquired whether the concomitants are general in nature (e.g., emotional or physical in nature) or are they more like neuromuscular, cardiac or gastrointestinal. Regardless of nature of questions raised, the questions are presented in different rows.

Table 1 shows an exemplar format of inquiries that would be posed to elicit responses from a client device user who wishes to treat an ailment (e.g., anxiety). A different series of inquiries may be developed if the ailment is severe (e.g., anxiety is severe or is characterized as a phobia). In other examples, instead of anxiety, inquiries may be directed to elicit responses to treat panic attacks. Also, different inquiries pertaining to different levels of panic attacks would be provided to the user.

A response, regardless of whether it is positive or negative, to a particular inquiry, in Table 1, may be relevant to whether one or more additional sets of inquiries are raised. In the event a response to a particular inquiry is relevant to a particular set of questions, then the set of questions are flagged or marked so that they are picked up to be implemented in a subsequent step. By way of example, Table 1 shows that if a response to a particular question is deemed relevant to a particular set of questions, then an "X" is placed under a column corresponding to the set of questions. As a result, one or more sets of questions relevant to treatment of an ailing individual are tracked in step 302.

It is important to understand that there is a difference between the terms "inquiry" or "inquiries" and the terms "question" or "questions," as they are used herein. The terms "inquiry" or "inquiries" refer to one or more queries, the response(s) to which lead to the identification of one or more relevant sets of questions that are used in a subsequent step (e.g., step 304). The terms "question" or "questions" also refer to queries, but serve a different purpose than the queries that fall within the category of "inquiry" or "inquiries." The answers to queries that fall into the category of "question" or "questions" facilitate selection of one or more remedies that may cure one or more of the ailments. Furthermore, to convey the concept of a reply to a query, the term "response" is used in connection with the terms "inquiry" or "inquiries" and the term "answers" is used in connection with the terms "question" or "questions."

As mentioned above, inquiries, as they are posed in Table 1, direct a user to certain sets of questions (also shown below in Table 2) that inform on which sets of questions are relevant to carry out a subsequent step. Although the algorithm presented in Table 1 and described herein is for addressing complaints of anxiety/phobias/panic attacks, the present teachings may similarly be used to design and deliver treatments for a wide variety of ailments, such as diarrhea, colic, teething, toothache, various injuries, motion sickness, influenza, abscesses, malaria, typhoid, cholera, dengue and hepatitis. The remedies of the present teachings are not just limited to human ailments, rather they extend to treating various animal/pet ailments.

In accordance with one embodiment of the present teachings, the series of inquiries, as presented in Table 1, are preferably simple yes/no and/or multiple choice inquiries and the second series of inquiries are of the same form as the first series of inquiries and may also include multiple-option multiple choice inquiries. The sets of inquiries that follow the second series of inquiries may be the same as the second series, but according to the present teachings, are contemplated to be multiple-option multiple-choice inquiries. In a multiple option-multiple choice inquiry, the multiple-choice inquiry offers none, one or more than one correct response. By way of example, a patient may respond to the following inquiry, "which of the following phobias or fears do you have: dark, heights, closed places, public speaking, spiders, snakes, birds, dogs, horses?" by checking none, one or more than one of the options.

In one alternate embodiment of the present teachings, before step 302 is carried out, the server receives a first series of responses from the client device. Then based on the answers received to the first series of inquiries, process 300 also includes providing a second series of inquiries to the client device. Consequently, process 300 includes providing, to the client device, multiple series of inquiries, wherein a subsequent series of inquiries may be based on the answers of a previous series of inquiries.

After the above-described step 302, a step 304 includes presenting, to the client device, one or more of the set of questions that are identified as relevant in the previous step. Then a step 306 is carried out. Step 306 includes receiving, from the client device, answers to one or more of the sets of questions.

Next, a step 308 also includes grading the answers, using one or more remedy appropriateness values to produce graded answers, and wherein a remedy appropriateness value quantifies clinical importance of remedy with respect to a question that is answered. In one implementation of the present arrangements, a logic engine has stored thereon the instructions for grading the answers received in step 306. According to one aspect, a logic engine may be part of a server that serves as a homeopathic logic engine and a homeopathic practitioner creates the underlying instructions and/or values that are stored on the logic engine. In accordance with one embodiment of the present teachings, the logic engine is created on an Excel sheet or similar branched-logic program. In other embodiments of the present teachings, the logic engine is created on an electronic spreadsheet, and not a physical spreadsheet. Instructions for grading include a grading scheme that uses a remedy appropriateness value. The remedy appropriateness value quantifies the clinical importance of a remedy with respect to a question (within a set of questions) that is answered. Clinical importance refers to the practical importance of a treatment effect—whether the remedy has a real genuine, palpable, noticeable effect on daily life of the ailing individual. In the context of homeopathic remedies, the term "clinical importance" refers to the treatment effect of a remedy on unique individuals with the same ailment. By way of example, ten people with fever might need ten separate remedies, one for each person, based on the unique profiles of how they answer the questions.

In one preferred embodiment of the present teachings, the grading scheme implemented in step 308 accounts for another parameter referred to as "question value". A question value quantifies importance of a particular question within a particular set of questions. According to this grading scheme, for each the question that is answered, the graded answer equals 1(QXR), where Q represents the question value and R represents the remedy appropriateness value. Similar to the remedy appropriateness value, a ques-

TABLE 2

| Questions | QA | Grade | Rescue Remedy ("RR") | RR test | Acon | Acon test | Arg-n | Arg-n test | Arn | Arn Test | Ars | Ars test |
|---|---|---|---|---|---|---|---|---|---|---|---|---|
| QS21 | | 1 to 5 | | | | | | | | | | |
| Anxiety upon doing new things? | | 2 | 1 | 0 | 1 | 0 | 3 | 0 | | 0 | 3 | 0 |
| Anxiety about taking exams? | 1 | 5 | 5 | 25 | 1 | 5 | 3 | 15 | | 0 | 2 | 10 |
| Anxiety about performance? | | 3 | | 0 | | 0 | 5 | 0 | | 0 | 3 | 0 |
| Anxiety when has success? | | 1 | | 0 | | 0 | 2 | 0 | | 0 | 2 | 0 |
| Anxiety about failing? | | 2 | 5 | 0 | 1 | 0 | 5 | 0 | 2 | 0 | 4 | 0 |
| Anxiety before or during public speaking? | | 5 | 5 | 0 | 1 | 0 | 5 | 0 | | 0 | 1 | 0 |
| Anxiety arising out of self-criticism? | | 2 | | 0 | | 0 | | 0 | | 0 | 2 | 0 |
| Total | | | | | | | | | | | | |

Table 2 shows one exemplar manner, in which step 308 is implemented. In this table, questions belonging to a set of questions, QS21 (deemed relevant in the example shown in Table 1). In this table, each question that belongs to QS21 is presented in a different row of a particular column. The different remedies under consideration, which may be as many as 120 or more in number, are presented as different column headings along a particular row. In this example, based on the answers to the different questions, the different remedies are graded from 1 to 5 based on their clinical importance. As shown in Table 2, a remedy appropriateness value is provided at a cell that intersects a particular row in which a question is posed and a remedy column, i.e., where values pertaining to a remedy are recorded. In this cell, the remedy appropriateness value is assigned based on the answers (received by the client device in step 306) to the question. As will be explained later, the remedy appropriateness value, which may be stored in memory, is used to ultimately arrive at a graded answer value. Although each of Tables 1 and 2 show a table as a spreadsheet, which may be in an excel format, the present teachings also contemplate formation of an electronic table. Regardless of whether a spreadsheet or an electronic table is constructed, based on the answers to the different questions in Table 2, the different remedies may be graded from 1 to 5 based on their clinical importance.

tion value for each question, within a set of questions, may also be stored in the logic engine.

With respect to grading, the example of Table 2 shows that in a column bearing the heading "QA," a positive answer to a question from the set of questions QS21 is recorded as "1". Specifically, a positive response was obtained for the question—"Anxiety about taking exams?" This question was assigned a question value of "5" selected from a range of values that span from 1 to 5. In one embodiment of the present teachings, a homeopathic practitioner assigns each question a question value and the remedy, based on the answers received, a remedy appropriateness value. In other embodiments of the present teachings, an individual that is not a homeopathic practitioner assigns the question value and the remedy appropriateness values. In one aspect of the present teachings, the question value may be a predefined number that is stored in the logic engine and is used for grading the answer. As mentioned above, a remedy appropriateness value, as it relates to the question raised, may be similarly assigned. For the same question, the remedy Acon, for example, is assigned a remedy appropriateness value of "1" selected from a range of values that spans from 1 to 5. Thus, for the remedy Acon, multiplying the number "1" by the product of 5 and 1 (which equals "5") arrives at a grade answer value of "5." In this manner, a graded answer for each remedy with respect to each question selected from a set of questions is preferably computed. Further, in Table 2, adjacent to a column entitled with a remedy name (hereinafter "remedy" column) is a column that has a title ending with the word "test," (hereinafter "remedy test" column), and the graded answer for the remedy is recorded in the remedy test column. Specifically, for the remedy Acon (which received a positive response), the graded answer value of "5" is stored in the Acon test column (i.e., the remedy test column for the remedy Acon). In one embodiment of the present teachings, the graded answer is stored in memory for use in a subsequent step.

In step 308, when both parameters—question value and remedy appropriateness value—are taken into account, various other schemes may be used for grading the answer. As another example the graded answer equals 1(Q+R), where Q represents the question value and R represents the remedy appropriateness value. Under this scheme, for the remedy Acon, multiplying the number "1" by the sum of 5 and 1 (which equals "6") arrives at a graded answer value of "6". As a result, any grading scheme may be used, so long as it is consistently for each graded answer to arrive at a score as described in step 310 below.

Step 310 includes scoring one or more remedies based on the graded answers to arrive at one or more remedy scores, and identifying one or more top remedies that have high remedy scores. A total score for each remedy with respect to a particular set of questions is obtained by adding the values of graded answers for each remedy (for all the questions that are answered in a particular set of questions). By way of example, all the values stored in a remedy test column (which correspond to a particular remedy) are added to arrive at a remedy score. In this manner, a total score for each remedy is obtained with respect to a particular set of questions. Stated differently, each set of questions has a total score with respect to particular remedy. In Table 2, there is a row entitled, "Total", where the total score for each remedy is presented. The remedy with the highest score is deemed "top remedy", and its identification is relevant in a subsequent step.

For a given set or sets of questions, when the total score of two or more top remedies is equal or substantially equal, then process 300 advances to another optional step that includes presenting an additional set of questions to the client device. This set of questions may be referred to as "confirmatories". Confirmatories are presented to the client device to break the tie or virtual tie in the score. Virtual tie refers to the case where the total scores for two or more remedies with respect to a particular set of questions are not exactly equal, but are close enough to be considered equal or within margin of error. To break a tie, process 300 also includes another optional step of obtaining answers to the confirmatories from the client device. Next, the confirmatory answers are graded, as explained above in connection with Table 2, and the remedies are scored, as explained above in connection with Tables 2 and 3, and the remedy with the highest total score is considered the top remedy or the best matched remedy for the ailing individual.

Regardless of whether confirmatories are used, in one embodiment of the present arrangements, a logic engine scores remedies by their relevance to the answers received from the client device. In other words, the logic engine scores the different type of remedies based on their therapeutic value in addressing a particular profile of answers to questions obtained in step 306. To this end, the answers provide insight into amelioration of that particular ailment in that particular person. If the remedy does not fit the profile of questions, then the remedy is considered to have no treatment effect.

Process 300 then proceeds to a step 312, which includes choosing, from a library of frequency files, one or more frequency files that correspond to one or more of the top remedies. A library of frequency files for different remedies may be created using extraction system 100 of FIG. 1, as described above. Such a library may be stored in memory, e.g., memory 213 of FIG. 2.

Finally, a step 314 includes presenting the frequency file as a remedy to the client device. In one embodiment, the frequency file of the present teachings is played at the client device. In other words, in response the answers are received from the client device, the appropriate frequency file is played at the client device. In an alternate embodiment, the frequency file is conveyed to the client device by email or some other mechanism, well known to those skilled in the art.

The frequency file is played for any duration and/or at certain periods (e.g., daily, weekly etc.) that is therapeutic. By way of example, duration is a time period that is between about 5 seconds and about 1 minute, and the frequency is any one member chosen from a group comprising certain times an hour, hourly, certain times a day, daily but ending after a certain number of days have lapsed.

Although illustrative embodiments of this invention have been shown and described, other modifications, changes, and substitutions are intended. By way of example, Tables 1-3 may be in electronic form and their layout in spreadsheet form is provided to show how data may be arranged electronically. Accordingly, it is appropriate that the appended claims be construed broadly and in a manner consistent with the scope of the disclosure, as set forth in the following claims.

What is claimed is:

1. A method of providing a remedy, said method comprising:
    identifying, based on responses to inquiries, one or more sets of questions that are relevant to one or more ailments and/or one or more unique expressions of said ailments, wherein a set of questions includes multiple questions;
    presenting, to a client device, one or more of said set of questions that are identified as relevant;
    receiving, from said client device, answers to one or more of said sets of questions;
    grading, using a logic engine that resides on a processor of said client device or a server, said answers using one or more remedy appropriateness values and a question value to produce graded answers, wherein a remedy appropriateness value quantifies clinical importance of a remedy with respect to a question that is answered, and said question value quantifies importance of a particular question within a particular said sets of questions, wherein for each said question that is answered, each of said graded answers equals an equation of $1(Q*R)$, and wherein said Q is a value of said question value and said R is a value of said remedy appropriateness value, and wherein said question value and said remedy appropriateness value are stored on the logic engine;
    scoring, using said logic engine, one or more different types of remedies based on said graded answers to arrive at one or more remedy scores and identifying one or more different types of top remedies that have high remedy scores;

choosing, from a library of frequency files, one or more frequency files that correspond to one or more of said different types of top remedies, wherein said library of frequency files include a library of digitized sound files, and said library of frequency files are stored on a memory of said client device and/or said server; and presenting said one or more frequency files as a remedy to said client device.

2. The method of providing a remedy of claim 1, wherein said identifying includes:

providing inquiries to said client device; and receiving, from said client device, response to said inquiries.

3. The method of providing a remedy of claim 2, wherein said providing inquiries includes providing inquiries in a tiered format.

4. The method of providing a remedy of claim 2, wherein said providing includes providing multiple sets of inquiries in different instances in time, and wherein a subsequent series of inquiries is provided based on answers responsive to a previous series of inquiries.

5. The method of providing a remedy of claim 1, wherein said remedy appropriateness value resides in said logic engine.

6. The method of providing a remedy of claim 1, wherein said question value resides in said logic engine.

7. The method of providing a remedy of claim 1, wherein said question value and said remedy appropriateness value are predefined value and/or assigned by a treatment provider.

8. The method of providing a remedy of claim 1, wherein said scoring includes adding up each of said graded answers to arrive at said remedy score.

9. The method of providing a remedy of claim 1, wherein said presenting said one or more frequency files includes transmitting a sound file that can be played at said client device.

10. The method of providing a remedy of claim 1, wherein said presenting said one or more frequency files includes producing a sound by playing said frequency file.

11. The method of providing a remedy of claim 1, wherein said choosing includes selecting said top remedy that has a highest score among said different types of remedies that are scored.

12. The method of providing a remedy of claim 1, wherein when each of the one or more different types of top remedies have a same remedy score, then said method of providing said remedy further comprises:

providing, to said client device, one or more confirmatory questions, which are different from one or more of said sets of questions;

receiving, from said client device, confirmatory answers to one or more of said confirmatory questions;

grading said confirmatory answers using said one or more of said remedy appropriateness values to produce graded confirmatory answers, and wherein each of said remedy appropriateness value quantifies clinical importance of a remedy with respect to a confirmatory question that is answered;

scoring said one or more different types of top remedies based on said graded confirmatory answers to arrive at a confirmatory top remedy score; and presenting, to said client device, a frequency file as a remedy, and wherein said one or more frequency files corresponds to said confirmatory top remedy score.

13. The method of providing a remedy of claim 10, wherein said presenting said one or more frequency files include playing said one or more frequency files for a specific duration and/or a specific frequency.

14. The method of providing a remedy of claim 13, wherein said duration is a time period that is between about 5 seconds and about 1 minute.

15. The method of providing a remedy of claim 13, wherein said frequency is played any one chosen from a group comprising a certain number of times per hour, hourly, certain times a day and daily.

* * * * *